United States Patent [19]

Smith

[11] Patent Number: 4,533,947

[45] Date of Patent: Aug. 6, 1985

[54] ADAPTABLE AREA FOR IMAGE STORAGE

[75] Inventor: Kendall A. Smith, Chagrin Falls, Ohio

[73] Assignee: Technicare Corporation, Solon, Ohio

[21] Appl. No.: 550,835

[22] Filed: Nov. 14, 1983

[51] Int. Cl.[3] .................................. A61B 6/02

[52] U.S. Cl. .................................. 358/111; 378/99; 378/901; 364/414; 382/6

[58] Field of Search .................. 378/901, 99, 100; 364/414; 358/111; 382/6

[56] References Cited

U.S. PATENT DOCUMENTS

| | | | |
|---|---|---|---|
| 4,044,240 | 8/1977 | Cox, Jr. et al. | 378/901 |
| 4,117,336 | 9/1978 | Bates | 364/414 |
| 4,434,503 | 2/1984 | Tanaka et al. | 382/48 |

*Primary Examiner*—Alfred E. Smith
*Assistant Examiner*—Charles F. Wieland
*Attorney, Agent, or Firm*—Audley A. Ciamporcero, Jr.; Michael A. Kaufman

[57] ABSTRACT

Method and apparatus for increasing the effective data storage transfer rate in a system to permit the recording of a rapid sequence of high resolution images by eliminating and hence not transferring designated portions of each image in the sequence.

6 Claims, 6 Drawing Figures

ADAPTABLE AREA FOR IMAGE STORAGE

TECHNICAL FIELD

This invention relates to X-ray imaging systems of the type having at least one large scale image memory where images acquired by a video camera are temporarily stored before being transferred to a storage medium such as disk and more particularly to reducing the amount of data transferred between the memory and disk.

BACKGROUND

Today many routine X-ray procedures involve the recording of a rapid sequence of images showing the passage of contrast material through a patient's arterial system. In order to accurately portray the blood flow in rapidly moving coronary arteries, a frame rate of 30 images per second is required. The level of detail desired in such images also mandates at least a 512×512 matrix size. Even higher matrix sizes, such as 1024×1024, are desirable for certain cerebral flow studies that are carried out at 4 to 8 frames per second. Both examples result in data volume that exceed conventional disk storage transfer rates. Thus, either the framing rate or the matrix size must suffer because of current limitations on the speed with which disk drives can transfer data. While the problem could be solved by increasing the number of disk drives utilized in a system, this is not a very practical solution because of the substantial additional expense that that introduces.

SUMMARY OF THE INVENTION

We have discovered a method and apparatus for increasing the effective data transfer rate between a digital image memory and a storage medium by recognizing that substantial portions of each image include irrelevant information which once identified can be effectively ignored. It has an automatic means of determining a reduced area of the image that must be stored for transfer. The system will examine the image received during a calibration operation and determine the actual extent of the relevant image information. This permits the data storage subsystem to adapt itself to the size and location of the relevant portion of the image and store only those matrix elements that contain relevant image data. This typically reduces the size of the image substantially and increases by an inversely proportional amount the image storage rate. In a preferred embodiment, a second memory is provided of comparable matrix size as the image memory where each matrix location in the second memory contains a single bit serving as a control element signalling whether or not the data value on the corresponding image memory location is to be transferred to/from disk.

DETAILED DESCRIPTION OF THE PREFERRED EMBODIMENT INCLUDING THE BEST MODE FOR CARRYING OUT THE INVENTION

For purposes of illustration only, the invention will be described in connection with a diagnostic X-ray system particularly well suited for high speed cardiac imaging known as the model DR-960 available from Technicare Corporation, Solon, Ohio 44139. While the invention will be described in the context of a digital radiographic system, it should be noted that the invention is applicable generally to any situation where large quantities of data must be transferred at high speed such as between a digital image memory and disk, but where some of the data may be eliminated because it adds no useful information.

Figure 1:
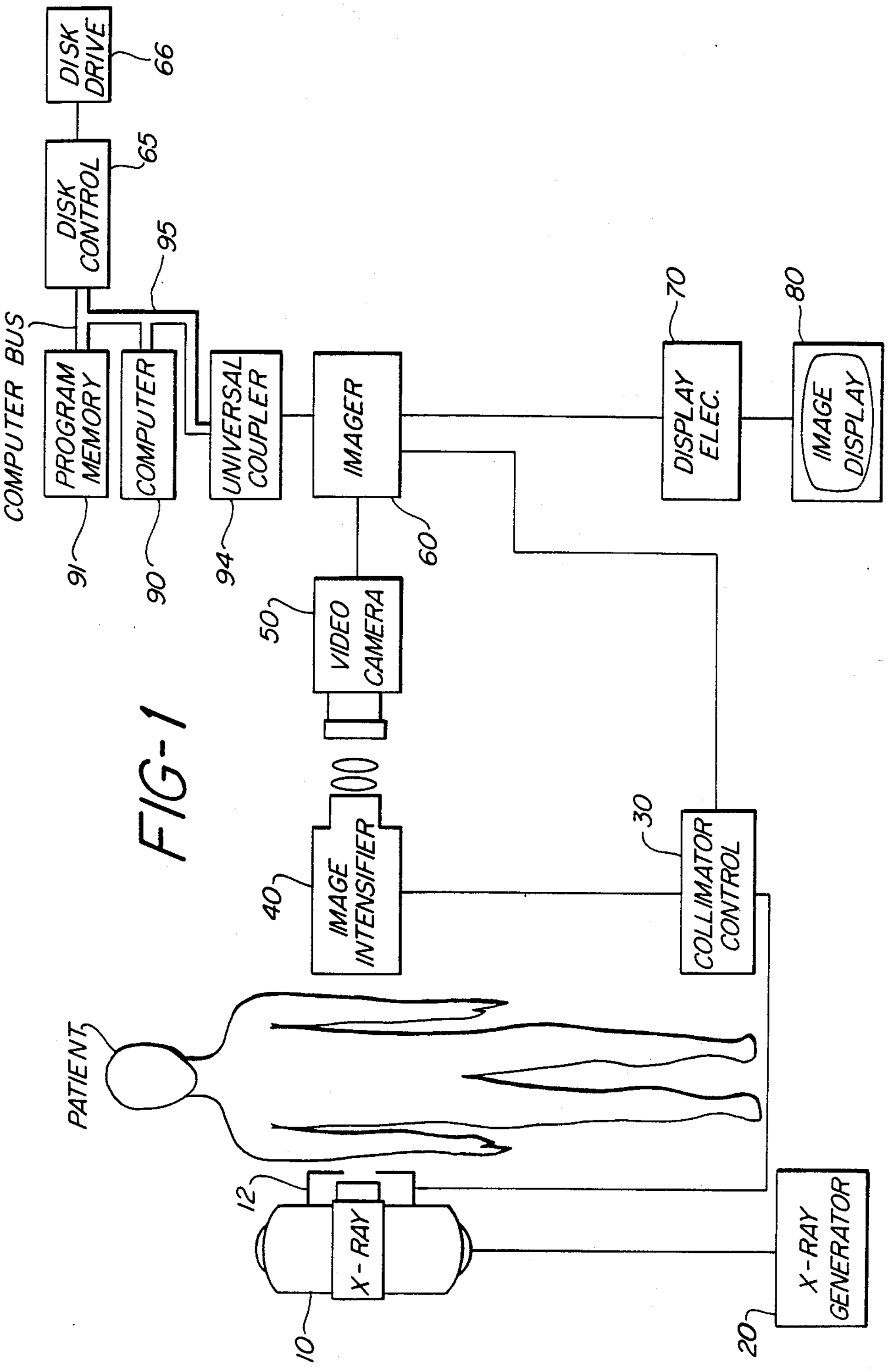
FIG. 1 is a block diagram of a digital radiographic system including a collimatable X-ray source, an image intensifier, a video camera, a digital image processing subsystem including an imager and video image display.
Figure 3:
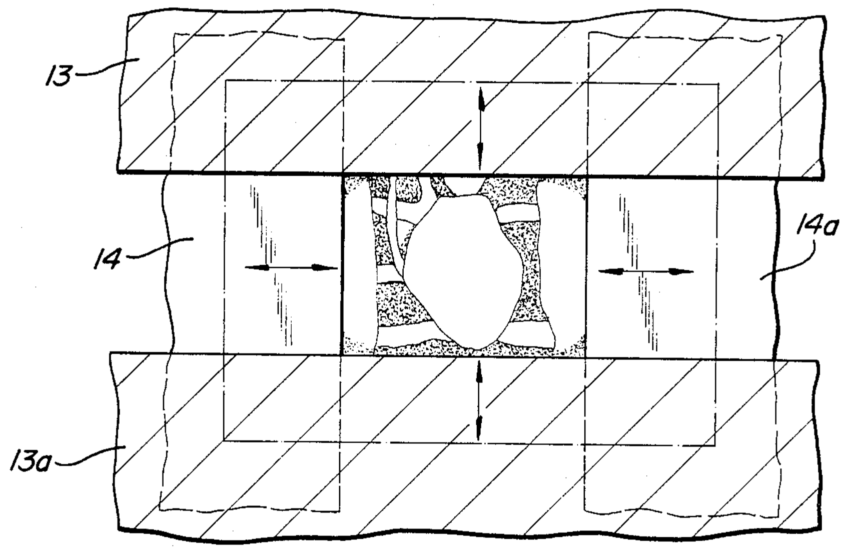
FIG. 3 is a schematic illustration of image area reduction by conventional collimation.

Referring now first to FIG. 1, the radiographic system includes a source of penetrating radiation such as an X-ray tube 10. Power for the X-ray tube is provided by X-ray generator 20. An adjustable collimator 12 is shown disposed adjacent the X-ray tube 10 to shape a beam of radiation emitted by the X-ray source and to minimize the radiation dose to the patient. The collimator typically includes two pairs of opposing straight edged lead blades 13, **13*a* and 14, 14*a* as shown in FIG. 3 or one having a variable, centrally positioned, iris-like circular opening such as collimator 19 shown in FIG. 4. With the system assembled, the collimator 12 is actually positioned on top of the X-ray tube and opens and closes to control the cross-sectional area of the X-ray beam striking a patient. The cross-sectional dimensions of the opening afforded by the collimator is defined by a collimator control 30**. As is readily apparent collimation can have a substantial reducing effect on the area of the imaging field having relevant information.

The system further comprises an image intensifier 40 which in known fashion receives radiation that has traversed the patient and converts such radiation into a two dimensional optical image. A television video camera 50 converts the optical image produced by the image intensifier into a video signal. The video signals are read frame by frame in raster fashion from the camera and processed in the imager 60 for subsequent storage or display on a TV image monitor such as image display 80 as controlled by means of display electronics 70. A contemporary digital radiographic system such as illustrated in FIG. 1 provides for the capture of a rapid sequence of images by a high quality television camera and the recording of these images on a digital storage device such as a magnetic disk.

Figure 2:
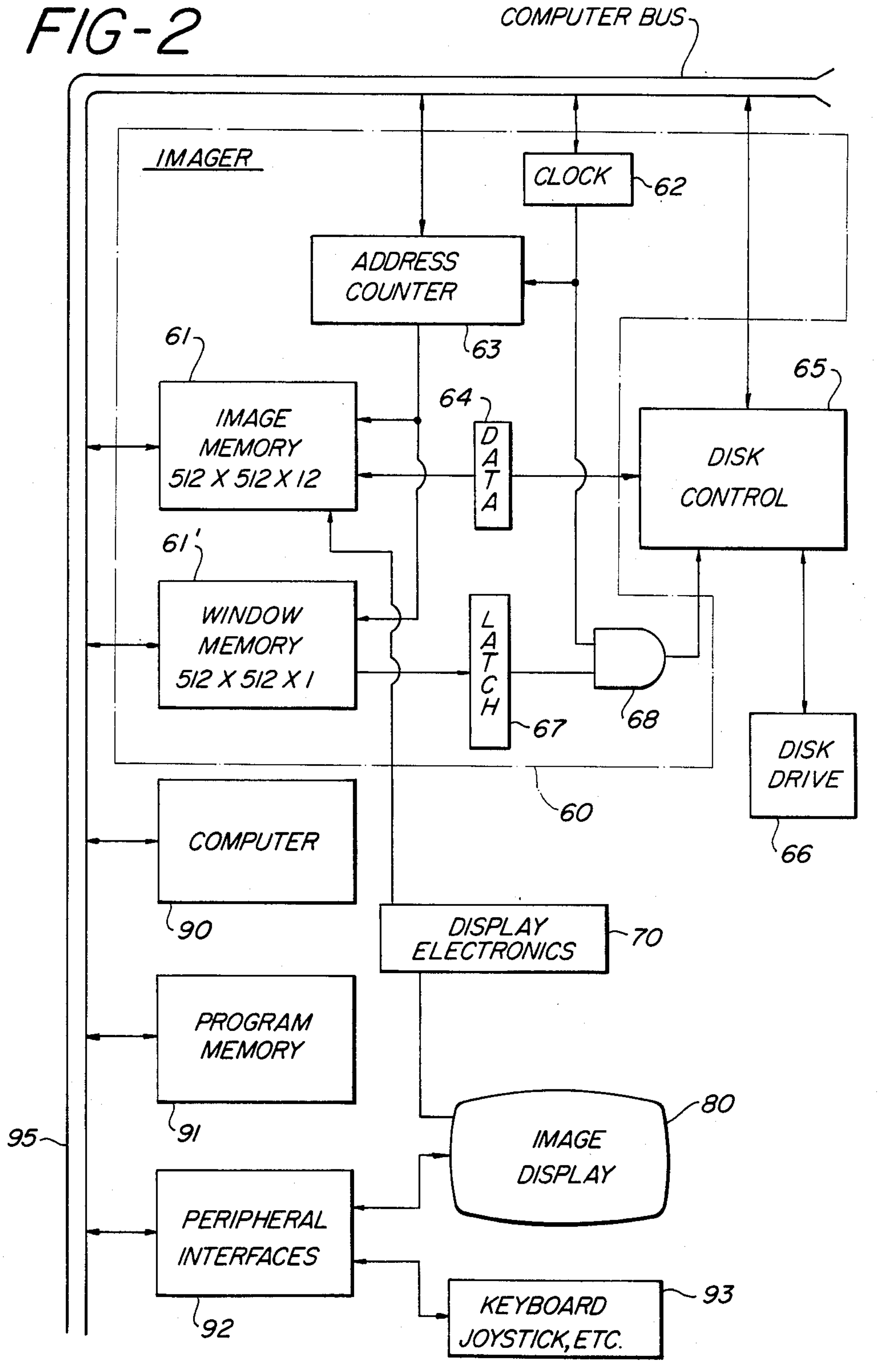
FIG. 2 is a more detailed block diagram of the digital electronic components of the system of FIG. 1 in accordance with the present invention.

FIG. 2 illustrates the relevant data paths in the digital portion of the system. It shows a computer 90 such as a PDP 11/23 which serves as the central processing unit. Communication between the computer and the other digital components described below is accomplished via input/output computer bus 95, which in turn is connected to a universal coupler 94. In addition to the imager 60, a program memory 91 and variety of peripheral interfaces 92 communicate with the computer.

Imager 60 includes at least one image memory 61 having a 512×512 matrix with 12 bits of data per pixel or matrix element. Image memory 61 thus has the capacity for storing $512^2$ words of data each 12 bits deep per image frame. Thus, if this memory were required to transfer all of the data it has the capacity to store 30 times per second, the system would be required to transfer on the order of 8 million 12 bit words per second between memory and disk, a rate well beyond current limits.

Conventional transfer of data in the image memory 61 is accomplished by means of a clock circuit 62 sending timed pulses to an address counter 63. As the pulses are received, the address counter generates sequential addresses corresponding to the image memory matrix. These addresses are transmitted to the image memory 61 to sequentially read out the value stored in each addressed matrix location. As each value is read from the memory, it is loaded into a data register 64. Normally, the clock pulse generated by clock circuit 62 is also applied directly (not shown) to a disk control circuit 65 which uses the pulse as a signal to load the value temporarily stored in the data register 64 and write it to disk 66 for storage. This technique is limited directly by the inherent data transfer rate constraint imposed by disk drive 66. Such a conventional data transfer subsystem is herein modified by the introduction of a second memory such as "window" memory 61' coupled to computer bus 95.

In a preferred embodiment the window memory 61' is of the same matrix size as the image memory so that each location in the window memory corresponds to one matrix location in the image memory 61. Each location in the window memory matrix contains a single bit such as a logical "1" or "0", each such bit signifying whether or not the corresponding image memory location data is to be transferred to/from disk or not. In operation, the clock pulse generated by the clocking circuit 62 and applied to address counter 63 is simultaneously transmitted to both memories 61 and 61' so that as the image memory reads the value from a particular location, the window memory will simultaneously read the particular control bit in the corresponding location. The control bit is then loaded into a register such as latching circuit 67. Thus, whenever a 12 bit data word appears in the data register 64 there also appears a single bit control word in latch 67. In the modified arrangement illustrated in FIG. 2, the clock pulse generated by the clock circuit 62 is also applied to a two input AND gate 68 rather than directly to disk controller 65. The second input to AND gate 68 is the control bit signal from latch 67. Thus, if the signal applied by latch 67 is a logical "0", indicative of no transfer, the clock pulse will not reach the disk controller, and the word loaded into data register 64 will not be written to disk 66. As the next clock pulse is generated by the clocking circuit 62, the value in data register 64 will be overwritten by the subsequent data value read from the image memory, and so on, until the window memory control bit loaded into latch 67 is a logical "1" which would permit the clock pulse to reach the disk controller 65. Since the time consumed by each clock pulse and logic decision is negligible relative to the time required for transferring a single word of data, the time required for the clocking mechanism is not a significant factor in calculating the data transfer rate. For all practical purposes, each matrix value not transferred can be considered a net savings proportional to the total number of matrix elements in the memory.

The same technique can also control transfers from disk 66 to the image memory 61. Thus, the same pattern of bits in the window memory 61' can selectively control both writing and reading of the image memory 61. This assures that image memory locations are read back in the same locations from where they are read.

Alternatively, the use of a window memory is avoided by dedicating one of the 12 bits in each matrix location of the image memory to a control function. This is feasible since 10 bits is typically sufficient to represent each data value in the image memory matrix. Under this alternative, each data value from the image memory would be sequentially read to the data register in response to a clock pulse, but the data register would not write to disk any word which, for example, had a zero as the most significant bit ("MSB"), where the MSB location would serve as the control function.

Another alternate implementation utilizes a window array of lower resolution i.e., smaller matrix size than the image memory array. In this modification one control bit would correspond to multiple image memory locations.

Alternatively the separate clocking circuit is eliminated and instead the address counter is clocked from the disk control 65 directly so that only those locations in the image memory with a corresponding true control bit in the window memory are transferred.

Another implementation replaces the window memory with another circuit that stores the desired pattern of control bits more compactly. Such a device stores a list of addresses corresponding to where the transfer of values are started and/or stopped. Another implementation calculates whether the location should be stored or not from its address. This permits eliminating from storage locations around the perimeter of an image, more than a specified radius from the center, etc.

Another implementation adds additional bits to each location in the window memory. A logic network is added to make logic decisions from a set of control bits for each location. A single logical value is output from this network and serves as the control bit. This permits multiple patterns to be stored and logical combinations specified as the control bit.

Figure 4:
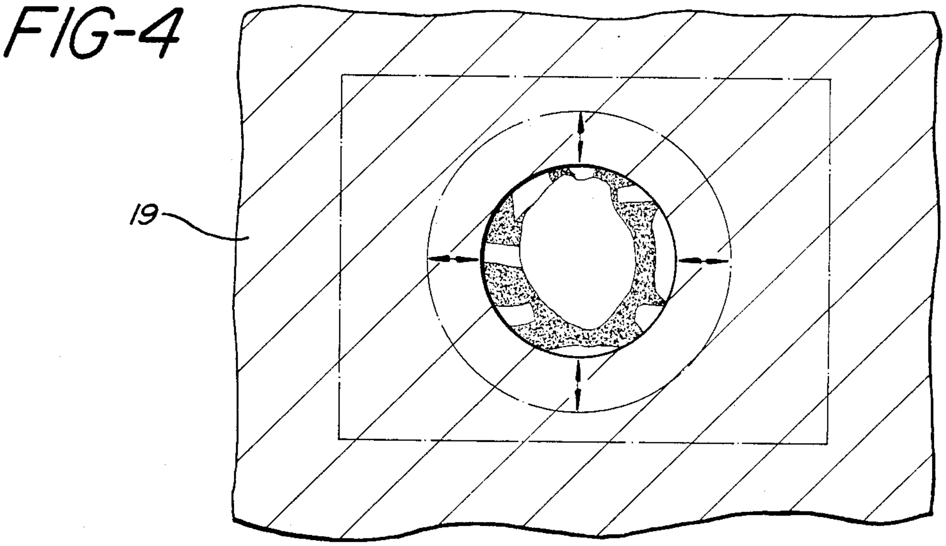
FIG. 4 is a view similar to FIG. 3 illustrating image area reduction by means of an iris type collimator.

In accordance with the best mode for carrying out the invention, the computer reads the image data values, searches through the image to determine the areas of no interest that are not to be transferred such as those covered by collimator blades illustrated in FIGS. 3 and 4 and writes into the image memory 61' the pattern of true and false control bits for the desired storage pattern.

Figure 5:
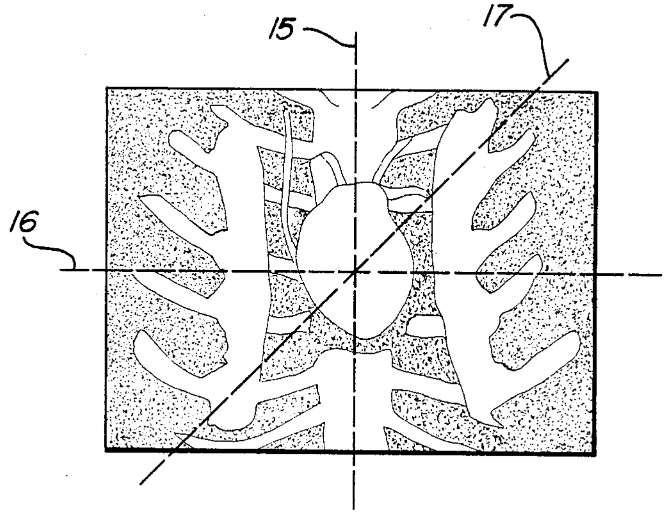
FIG. 5 is a pictorial illustration showing a scheme for rapidly determining the location of collimator blades relative to an image display.
Figure 6:
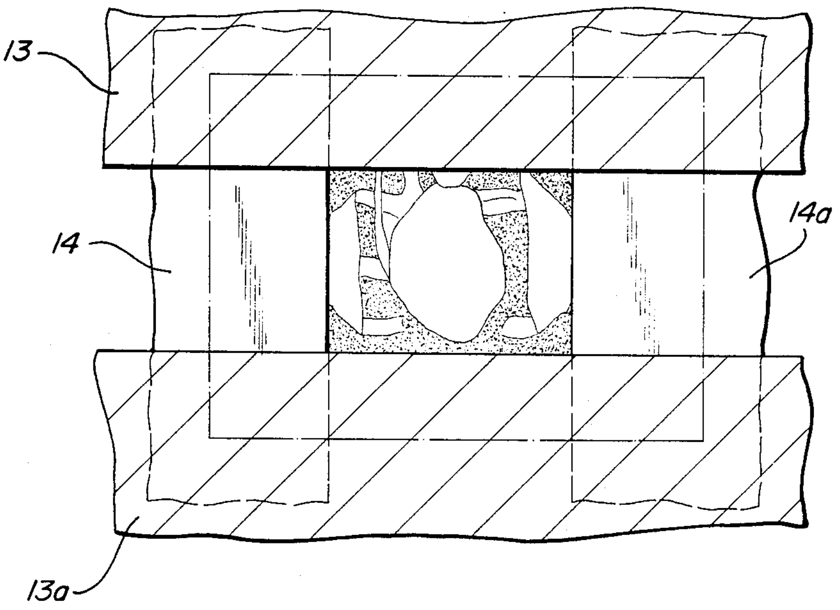
FIG. 6 is a pictorial depiction representative of increased area reduction by combination of rectangular collimation and operator drawn area reduction.

FIG. 5 shows a scheme for rapidly determining the location of the collimator blades by examining selected cross-sectional lines 15, 16, and 17 in the image. When the collimator is known to be a rectangular or circular, centered aperature type, only these lines need to be examined to locate the image area. In the case of a more irregular collimator opening, the entire image can be examined, pixel by pixel, to identify those pixels that, because they recorded little or no X-ray exposure, can be discarded from the image being stored. In addition to the portions of the image covered by collimator blades, the operator can designate additional areas to be eliminated from storage as shown, for example, in FIG. 6. These areas may be corners of the noncollimated portion of the image or other areas of obvious low interest background. These areas can be marked in conventional fashion by use of, for example, a joy stick 93 through peripheral interfaces 92 in conventional fashion.

In general, the greater the portion of the image matrix that can be ignored, the greater the proportional savings in the time required for data transfer. Thus, if the combination of the collimator blade covered portions and the operator drawn areas eliminates 75 percent of the available image area, only 25 percent or one quarter of the matrix values need be transferred, resulting in a four fold increase in the effective data transfer rate. In short, the fraction of the image area that is to be transferred yields a data transfer rate increase on the order of the inverse of such fraction. This permits either a higher framing rate for a particular study or the use of a higher resolution matrix without adding any significant cost to the system. The system may include a real-time display of the potential framing rate for the operator to examine as the collimator adjustments are being made. This allows the operator to adjust the blades such that a particular, desired, framing rate is achieved.

What is claimed is:

1. In a radiographic imaging apparatus of the type having a computer controlled image memory for storing a large matrix image whose contents are transferrable to a storage medium, a system for reducing data transfer between said memory and said storage medium without degrading image quality comprising:

(a) a window memory means of preselected matrix size;

(b) means for generating in said window memory means an array of control bits, each corresponding to at least one matrix element in the image memory wherein each of said bits designates either acceptance or deletion of the corresponding matrix element in the image memory; and (c) means connected to both the image memory and said window memory for transferring to the storage medium only data from the image memory which are stored in matrix elements having an acceptance bit in the corresponding matrix elements in the window memory means.

2. In the system according to claim 1 wherein said window memory means has an m×n array of control bits such that each bit in the window memory means corresponds to image data in one corresponding address in the image memory.

3. In the apparatus according to claim 1 wherein said means for transferring includes an AND gate.

4. In the radiographic imaging apparatus of claim 3 further comprising clocking means in data communicating relationship with the image memory and said AND gate for serially transferring selected data between said image memory and said storage medium.

5. In a radiographic imaging apparatus of the type having a computer controlled digital image memory for acquiring and processing in sequence frames of digitized images which are transferrable to a storage medium, said memory comprising m×n matrix elements each capable of storing a digital value, the improvement comprising:

(a) means for identifying at least one variable portion of said image memory having relatively low information content, wherein said portion includes at least one matrix element; and (b) means responsive to said identifying means for prohibiting from transferring between said image memory and said storage medium all image data values stored in matrix elements within said identified portion thereby reducing data transfer between said memory and said storage medium without degrading image quality.

6. A method for reducing data transfer between a digital image memory and an associated storage medium in a real time dynamic radiographic imaging system comprising the steps of:

(a) acquiring and digitizing a first radiographic image;

(b) loading said first radiographic image into a digital memory for subsequent data processing and display on a video monitor;

(c) performing a calibration to identify areas of the image of relatively low information relevance;

(d) acquiring in sequence a series of radiographic images of an object, converting said images into an array of digital data values, and sequentially loading each image into a digital memory; and (e) transferring from said image memory to the storage medium only those data values in said image memory that are located outside the identified areas.

* * * * *